United States Patent
Skinner et al.

(10) Patent No.: US 10,954,187 B2
(45) Date of Patent: Mar. 23, 2021

(54) PROCESS FOR PRODUCTION OF AMMONIA AND DERIVATIVES, IN PARTICULAR UREA

(71) Applicant: Casale SA, Lugano (CH)

(72) Inventors: Geoffrey Frederick Skinner, Reading (GB); Raffaele Ostuni, Lugano (CH)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 15/508,758

(22) PCT Filed: Aug. 5, 2015

(86) PCT No.: PCT/EP2015/068019
§ 371 (c)(1),
(2) Date: Mar. 3, 2017

(87) PCT Pub. No.: WO2016/034355
PCT Pub. Date: Mar. 10, 2016

(65) Prior Publication Data
US 2017/0283371 A1  Oct. 5, 2017

(30) Foreign Application Priority Data
Sep. 5, 2014 (EP) .................................. 14183753

(51) Int. Cl.
*C07C 273/10* (2006.01)
*C01C 1/04* (2006.01)
(Continued)

(52) U.S. Cl.
CPC .............. *C07C 273/10* (2013.01); *B01J 7/00* (2013.01); *C01B 3/025* (2013.01); *C01C 1/0405* (2013.01);
(Continued)

(58) Field of Classification Search
CPC .... B01J 7/00; C01B 3/025; C01B 2203/0233; C01B 2203/0244; C01B 2203/0255;
(Continued)

(56) References Cited

U.S. PATENT DOCUMENTS 3,162,242 A * 12/1964 Profos ..................... F22B 35/10
165/293
3,705,009 A    12/1972 Dougherty
(Continued)

FOREIGN PATENT DOCUMENTS

CA       2831183    *  9/2012
EP       2065337 A1    6/2009
(Continued)

OTHER PUBLICATIONS

Dhungel, "Waste Heat to Power Systems," CHP—Combined Heat and Power Partnerships, 2012, pp. 1-9 (Year: 2012).*
(Continued)

*Primary Examiner* — Amy C Bonaparte
(74) *Attorney, Agent, or Firm* — Akerman LLP

(57) ABSTRACT

A process for producing ammonia and a derivative of ammonia from a natural gas feed comprising conversion of natural gas into a make-up synthesis gas; synthesis of ammonia; use of said ammonia to produce said derivative of ammonia, wherein a portion of the natural gas feed is used to fuel a gas engine; power produced by said gas engine; is transferred to at least one power user of the process, such as a compressor; heat is re-covered from exhaust gas of said gas engine; and at least part of said heat may be recovered as low-grade heat available at a temperature not greater than 200° C., to provide process heating to at least one thermal user of the process, such as CO2 removal unit or absorption chiller; a corresponding plant and method of modernization are also disclosed.

22 Claims, 1 Drawing Sheet

(51) Int. Cl.
*C01B 3/02* (2006.01)
*B01J 7/00* (2006.01)
*F01N 5/02* (2006.01)

(52) U.S. Cl.
CPC .......... *C01C 1/0452* (2013.01); *C01C 1/0488* (2013.01); *F01N 5/02* (2013.01); *C01B 2203/0233* (2013.01); *C01B 2203/0244* (2013.01); *C01B 2203/0255* (2013.01); *C01B 2203/0283* (2013.01); *C01B 2203/0288* (2013.01); *C01B 2203/0415* (2013.01); *C01B 2203/0475* (2013.01); *C01B 2203/068* (2013.01); *C01B 2203/0894* (2013.01); *C01B 2203/142* (2013.01); *C01B 2203/84* (2013.01); *Y02P 20/10* (2015.11); *Y02P 20/129* (2015.11); *Y02P 20/52* (2015.11)

(58) Field of Classification Search
CPC .... C01B 2203/0283; C01B 2203/0288; C01B 2203/0415; C01B 2203/0475; C01B 2203/068; C01B 2203/0894; C01B 2203/142; C01B 2203/84; C01C 1/0405; C01C 1/0452; C01C 1/0488; C07C 273/10; F01N 5/02; Y02P 20/123; Y02P 20/129; Y02P 20/13; Y02P 20/52
See application file for complete search history.

(56) References Cited

U.S. PATENT DOCUMENTS

| | | | | |
|---|---|---|---|---|
| 4,479,925 | A | 10/1984 | Shires et al. | |
| 5,229,102 | A | 7/1993 | Minet et al. | |
| 5,281,403 | A * | 1/1994 | Jones | B01D 53/8625 423/235 |
| 6,632,846 | B2 * | 10/2003 | Sheppard | C07C 1/0485 423/359 |
| 8,268,024 | B2 * | 9/2012 | Price | B01J 8/04 422/625 |
| 2010/0132259 | A1 * | 6/2010 | Haque | C01B 3/025 48/62 R |
| 2016/0115017 | A1 | 4/2016 | Ostuni et al. | |
| 2017/0152218 | A1 | 6/2017 | Ostuni et al. | |
| 2017/0283371 | A1 * | 10/2017 | Skinner | C01B 3/025 |

FOREIGN PATENT DOCUMENTS

| | | |
|---|---|---|
| EP | 2 690 089 A1 | 1/2014 |
| GB | 1272369 A | 4/1972 |
| GB | 2146632 A | 4/1985 |
| RU | 2283832 C2 | 9/2006 |

OTHER PUBLICATIONS

Chapman, "Performance, Efficiency, and Emissions Characterization of Reciprocating Internal Combustion Engines Fueled with Hydrogen/Natural Gas Blends," Final Technical Report, Mar. 2008, pp. 1-70. (Year: 2008).*

Gupta, "Natural Gas Fired Reciprocating Engines for Power Generation: Concerns and Recent Advances," Natural Gas—Extraction to End Use, pp. 211-234. (Year: 2012).*

Hiller ("Gas Production, 1. Introduction" Ullmann's Encyclopedia of Industrial Chemistry, Oct. 15, 2011, downloaded from https://onlinelibrary.wiley.com/doi/full/10.1002/14356007.a12_169.pub3, on Oct. 29, 2019, p. 403-421) (Year: 2011).*

International Search Report issued in connection with PCT/EP2015/068019.

International Preliminary Report on Patentability issued in connection with PCT/EP2015/068019.

Akorede, M. et al., "Distributed Energy Resources and Benefits to the Environment", Renewable and Sustainable Energy Reviews, Elseviers Science, New York, New York, vol. 14, No. 2, Feb. 1, 2010, pp. 724-734.

Vasilios Konstantakos et al., "A Decision Support Model for Combined Heat and Power Economic Evaluation", Applied Thermal Engineering, PergamonOxford, Great Britain, vol. 42, Mar. 9, 2012, pp. 129-135.

Sahafzadeh et al., "Integration of a gas turbine with an amonia process for improving energy efficiency", Applied thermal engineering, Pergamon, Oxford, GB (May 15, 2013), vol. 58, No. 1—p. 594-604.

* cited by examiner

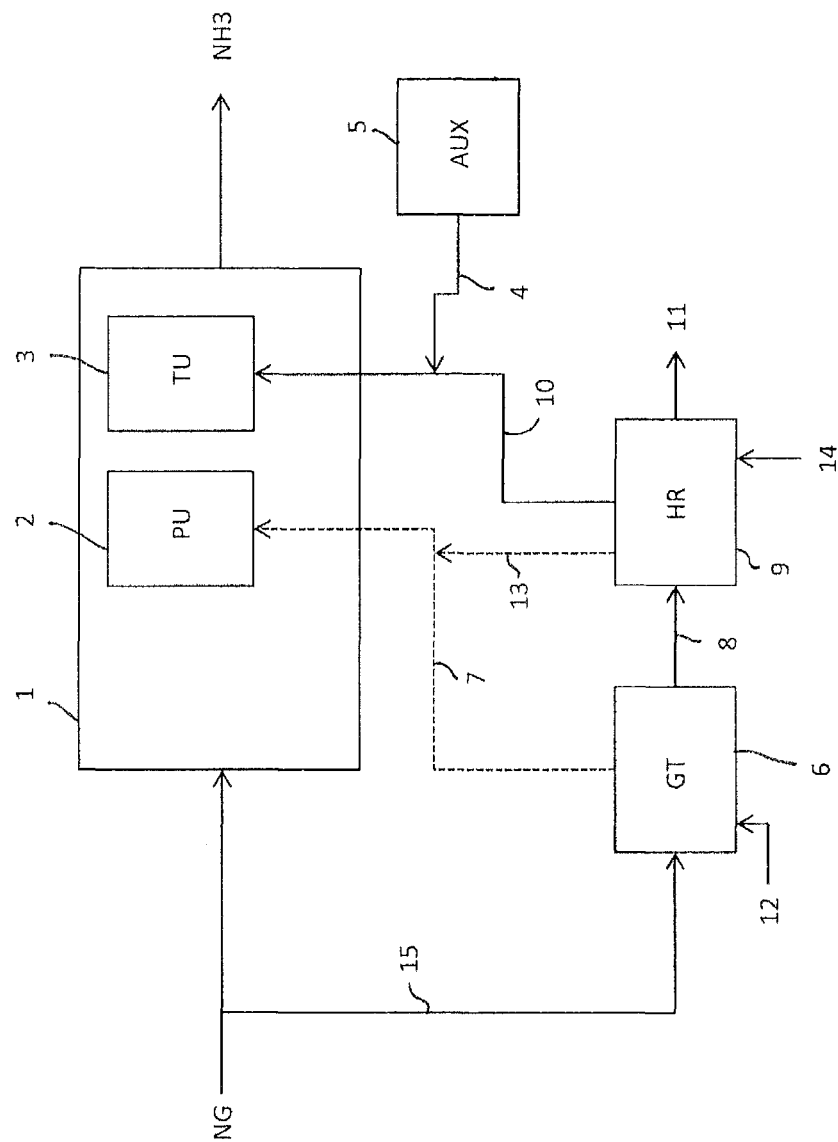

PROCESS FOR PRODUCTION OF AMMONIA AND DERIVATIVES, IN PARTICULAR UREA

This application is a national phase of PCT/EP2015/068019, filed Aug. 5, 2015, and claims priority to EP 14183753.4, filed Sep. 5, 2014, the entire contents of both of which are hereby incorporated by reference.

FIELD OF APPLICATION

The invention concerns a method for producing ammonia and derivatives of ammonia, particularly urea, starting from natural gas. The invention also discloses a method of modernizing an ammonia-urea plant.

PRIOR ART

The integrated production of ammonia and derivatives of ammonia is known in the fertilizer industry. For example the production of ammonia and urea is known.

Ammonia production, usually from a natural gas feed, involves conversion the natural gas into a synthesis gas in a front-end section and the conversion of said synthesis gas into ammonia in a synthesis loop. The conversion of the natural gas feed into synthesis gas usually involves two-stage steam reforming, although autothermal reforming and partial oxidation are feasible options, followed by purification including shift conversion of CO to CO2, removal of CO2 and optionally methanation. The resulting purified gas is termed ammonia synthesis gas. A process for producing ammonia synthesis gas is described for example in EP 2 065 337.

In a so-called ammonia-urea plant, at least part of the synthesized ammonia is reacted with carbon dioxide to produce urea.

A plant for the production of ammonia and its derivatives comprises also a complex steam system including both steam producers and steam users. The steam producers recover process heat from various process streams, mostly from conversion of the natural gas feed into generation of raw synthesis gas (usually by steam reforming) and from its subsequent purification. The steam users include for example one or more steam turbines to drive equipment such as compressors.

The main steam users of an ammonia-urea plant are the driving turbines of large gas compressors such as the synthesis gas compressor which raises the pressure of the generated make-up gas to the pressure of the synthesis loop, and other compressors for process air, ammonia, carbon dioxide or natural gas.

The steam system uses typically a Hirn cycle (or superheated steam Rankine cycle) to produce power. Said cycle as applied in ammonia plants however is relatively inefficient, with less than 30% efficiency and typically only 26-27% even for relatively modern and large plants. Hence, less than 30% of the heat used to raise/superheat the steam is converted into mechanical power, with more than 70% lost mainly to air/water cooling in the steam condenser and in other inefficiencies.

A part of the steam produced in the steam system is also used in the reforming process. This fraction of steam is called process steam. A relevant parameter of the reforming process is the steam-to-carbon ratio which is the molar ratio between steam and carbon introduced in the process. Said ratio is normally around 3.

The steam generated by process heat recovery is generally not enough to cover all requirements, and the shortfall is covered in the prior art by inclusion of a gas-fired auxiliary boiler to generate the additional steam required. Said boiler introduces however an additional consumption of natural gas, increasing the overall consumption for a given capacity in terms of ammonia which is synthesized. Said additional consumption is a drawback especially in a location where the natural gas is expensive and/or is available in a limited amount.

Existing and new plants in these areas of high natural gas cost must minimize the consumption of natural gas to be competitive on the global fertilizer market. Moreover, where the total natural gas available for fertilizer production is limited, any reduction in the specific gas consumption of the plant enables a corresponding increase of the fertilizer production capacity.

The main natural gas consumer of a fertilizer complex for the production of a derivative of ammonia, such as urea, is the ammonia plant. Although many efforts have been made to reduce the energy consumption of ammonia plants, the processes available today are not efficient enough, or are too expensive to operate, where gas costs are high. Even more so, the existing methods for revamping existing ammonia plants are not competitive as they generally address the requirement to increase the capacity of existing units rather than minimizing the gas consumption.

In recent times, limitations of quantity of natural gas available for the ammonia plants have emerged. Such limited availability may comprise a physical gas shortage due to the reduction of the production of the gas fields, or may be due to commercial and/or economic reasons like running out of the contractual share of gas available to the plant and/or a different scenario of price and demand for natural gas.

In addition to the above-mentioned large compressors, a conventional ammonia or ammonia-urea plant typically contains several smaller rotating machines, such as small compressors, fans and pumps. Historically these smaller machines have been directly driven by steam turbines having a low efficiency. In a few existing ammonia plants, some small steam turbines have been replaced with electric motors in order to reduce operating costs, while in some new plant designs most or all of the smaller machines are electrically driven, with the necessary power provided by a central generator driven by a more efficient steam turbine. Even in the case of those new plants designs, however, the overall fuel-to-power thermal efficiency for driving the smaller machines is less than 30%.

Hence there is still the need to increase the fuel-to-power efficiency of the driving system of the various machines (including the smaller compressors, fan and pumps) of ammonia plants.

SUMMARY OF THE INVENTION

The problem faced by the invention is to solve the above drawbacks and reduce the energy consumption of the ammonia plants based on natural gas feed. In particular, a purpose of the invention is to reduce the amount of natural gas which is consumed in gas-fired boilers to generate steam required by the power users of the plant.

The idea underlying the invention is to furnish at least part of the power demanded by the smaller rotating machines, such as small gas compressors, fans, pumps by means of reciprocating gas engines.

Accordingly, the above problem is solved by a process for producing ammonia and a derivative of ammonia from a natural gas feed, according to claim 1.

The term of reciprocating gas engine, in this description, denotes a reciprocating internal combustion engine comprising one or more reciprocating pistons inside respective cylinders. Said gas engine operates on 2-stroke or 4-stroke cycle, and is fuelled with a gaseous fuel such as for example natural gas.

Reciprocating gas engines are available with fuel-to-power thermal efficiency of 45-50%. Then, the provision of power to the said smaller rotating machines by said gas engine(s) in substitution for steam turbines will enable a reduction in the quantity of steam generated in the above-mentioned auxiliary steam boiler. As the fuel-to-power thermal efficiency of the gas engine(s) is higher than for the corresponding steam cycle, there will result a significant saving in the natural gas consumption of the whole ammonia or ammonia-urea plant.

Power produced by the gas engine can be transferred to the users by an electric motor using electricity produced by the gas engine, while mechanical coupling, (for example by means of a fluid coupling) may also be used. At least some of the heat contained in the exhaust of said gas engine is recovered for use in the thermal users of the plant. Heat contained in the coolant of the gas engine may also be used in the plant as a low-grade heat.

The term of low-grade heat denotes heat which is made available to the thermal users at a temperature of 200° C. or less. According to the invention, said low grade heat is recovered by means of a suitable heat exchange medium (also termed heat sink fluid) which is indirectly heated by the exhaust gas of the gas engine to a temperature which is not greater than 200° C. Said heat exchange medium may be, for example, water which is heated or partially or completely evaporated.

A preferred feature of the invention is a regulation of the global steam-to-carbon ratio (SC ratio) of the front-end section to a value lower than conventional. Preferably said SC ratio is regulated to a value of less than 2.7 and more preferably in the range 2.3 to 2.6. Although lowering the SC ratio has certain advantages for the ammonia production process as outlined below, it has the disadvantage of determining a reduction in the quantity of steam available from heat recovery for power generation; this shortfall is however compensated in the present invention by the provision of said gas engine. Hence, the advantages of a lower SC can be fully exploited.

Beneficial effects of a low SC ratio include: the steam required for the reforming process is reduced; the heat duty of the steam reformer for preheating and reforming the mixed feed is reduced for a given ammonia production, and so is the reformer fuel consumption; less heat is rejected to cooling water/air at the end of the heat recovery train in the front end, after recovering the valuable heat from the syngas (steam is in fact added in large excess of steam the requirements for the reforming and CO shift, and the excess steam is substantially all condensed before the synthesis); and the mass flow rate in the front end is lower.

Preferred ways of facilitating a reduction in the SC ratio include provision of a pre-reformer and use of improved catalysts in the steam reformer and CO shift reaction stages.

According to the invention, heat, particularly low-grade heat, is recovered from exhaust of said gas engine. Said heat can be used for a number of purposes including, but not limited to, the following examples: heating of a heat transfer medium such hot water or thermal oil, the regeneration of a CP2-rich solution in a CO2 removal unit, the heating of the reboiler of an absorption refrigeration chiller, the distillation of an ammonia-rich aqueous ammonia solution, and/or the initial preheating of natural gas, process air, combustion air.

According to different embodiments, said low-grade heat as defined above constitutes only a portion of the total heat that can be recovered from the exhaust of the gas engine. Heat recovered from the gas engine exhaust at a higher temperature, for example an exhaust temperature greater than around 250° C., may be used for example for the generation or superheating of steam suitable to drive a turbine. One embodiment of the invention provides that: a first portion of heat recovered from exhaust of said gas engine is used in a heat recovery steam generator to produce superheated steam and said steam is expanded in a back-pressure or extraction steam turbine producing further mechanical power, thus forming a combined cycle, and a second portion of heat recovered from exhaust of said gas engine is used to provide said low-grade heat. More preferably, a steam flow taken from said backpressure or extraction steam turbine can be further used to provide heating to at least one of said thermal users.

Part of the steam produced can also be exported if an external user is available.

According to some embodiments of the invention, part of the fuel for the gas engine is a waste fuel stream. For example a waste fuel stream for the gas engine may include: a purge gas taken from said ammonia synthesis loop, or a tail gas from a loop purge recovery unit. Said unit for example recovers hydrogen from a purge gas which is withdrawn from the ammonia synthesis loop. This is another advantage and synergistic effect of the invention, because the purge gas from the ammonia synthesis loop can be used as fuel in the gas engine, even if at low pressure.

The heat recovered from exhaust gas may provide direct or indirect heating to the thermal users, according to the various embodiments of the invention. Indirect heating may comprise for example the heating of a suitable heat transfer medium or the pre-heating of selected streams such as pre-heating of fuel or pre-heating of combustion air of a fired reformer.

An exemplary embodiment of direct heating is direct use of exhaust gas from said gas engine as combustion medium (gas stream containing oxygen), in a fired reformer or other fired heater. Accordingly, the heat of the exhaust gas is directly transferred to the combustion process, in a manner which is energetically equivalent to pre-heating of fuel or of combustion air.

The invention is synergistic in particular with carbon dioxide removal techniques which require a low-grade heat. For example, removal of carbon dioxide by chemical or chemical-physical absorption needs a heat input used for regeneration of a CO2 removal solution. Said solution may include amine or potassium carbonates or similar.

The above mentioned derivative of ammonia may be, for example, one or more of urea, phosphates or nitric acid. Preferably said derivative is urea. A preferred application of the invention relates to ammonia-urea processes and plants, where some or all of the synthesized ammonia is reacted with carbon dioxide to produce urea.

Another aspect of the invention is a method of modernizing a plant for producing ammonia and a derivative of ammonia, particularly urea, according to the attached claims.

Said method is characterized by the provision of: at least one reciprocating gas engine; suitable power transfer means to transfer the power produced by said engine to at least one of the power users; heat recovery means for recovering heat, particularly low-grade heat, from the exhaust gas of said gas engine, and also comprises the provision of said low-grade heat to at least one of the thermal users of the plant, or to at least one newly-installed thermal user.

In some embodiments, the modernization comprises the installation of new thermal users. A newly-installed thermal user, in some embodiments, may replace an existing power user. For example, the ammonia section normally comprises a vapour compression refrigerator for condensation of the produced ammonia, and the invention may comprise the replacement of said cycle with an absorption refrigerator which uses low-grade heat instead of mechanical power.

Hence, an aspect of the invention is to provide a suitable low-grade heat sink, to exploit the heat recovered from the gas engine exhaust. This may be done by lowering the steam-to-carbon ratio, as stated above, and/or by installing new thermal users.

An advantage of the invention is that the gas engine alone can reach a thermal efficiency of more than 45% on LHV (low heat value of fuel) basis, and an efficiency of over 50% can be achieved when a heat recovery steam generator (HRSG) and associated back-pressure or extraction steam turbine, as described above, are also provided. These efficiency values are considerably higher than the typical efficiency of the steam cycle in an ammonia plant, resulting in a reduction of consumption of natural gas fuel and hence in the total gas consumption of the ammonia plant.

Another advantage is the strong integration and unexpected synergistic effect between the provision of said power unit, the lowering of the SC ratio, and the feeding of low-grade heat to the existing or newly-installed thermal users.

The invention is particularly advantageous in conjunction with chemical or chemical-physical absorption technique for the removal of carbon dioxide. A $CO_2$ removal unit with chemical or chemical-physical absorption is a major user of low-grade steam; the remaining steam after abstraction of steam needed for $CO_2$ solvent regeneration can be exported, but the amount exportable is generally limited. Reducing the SC ratio has the effect that less steam (i.e. less amount of low grade heat) is available, which would be perceived as a drawback in the prior art. This drawback could be theoretically solved by implementation of a physical absorption $CO_2$ removal unit, which would require less heat for solvent regeneration than a chemical or chemical-physical $CO_2$ removal unit, but this would entail a significant capital cost. The invention overcomes this problem, thanks to the possibility to recover $CO_2$ removal solvent regeneration heat from exhaust gas of the gas engine.

The invention will be further elucidated by the following description of an embodiment thereof, given by way of non-limiting example with reference to the attached FIG. 1.

DETAILED DESCRIPTION

FIG. 1 illustrates a scheme of a process for ammonia synthesis from natural gas, according to a preferred embodiment of the invention.

Block 1 denotes an ammonia-urea plant comprising: an ammonia synthesis section, comprising a front end section and a high pressure synthesis loop, and a urea plant where some or all of the ammonia is reacted with carbon dioxide to produce urea.

Said front end section comprises preferably a steam reforming section and a purification section. Said steam reforming section comprises for example a primary steam reformer and a secondary reformer. Said purification section may include shift converters of CO to $CO_2$, a $CO_2$ removal unit and, optionally, a methanator.

The ammonia-urea plant 1 comprises a number of power users 2 and thermal users 3. Said power users (PU) include gas compressors, fans and pumps. Thermal users (TU) typically use steam as a source of heat and include for example the $CO_2$ removal unit where heat is needed for regeneration of a $CO_2$ removal solution.

A portion 15 of the available natural gas feed NG is used to fire a reciprocating gas engine 6, including a plurality of cylinder-piston assemblies.

The power produced by said gas engine 6 is transferred to one or more of the PUs (line 7) in electrical or mechanical form, that is via conversion into electrical energy or direct mechanical coupling.

For example, in a first embodiment a PU such as a pump is powered by an electric motor powered at least in part by electrical energy produced by a generator driven by said gas engine 6; in a second embodiment said PU is mechanically coupled to said gas engine.

The power produced by gas engine(s) 6 hence will replace one or more of the steam turbines of the prior art.

Exhaust gas flow 8 discharged by said gas engine 6 is fed to a heat recovery unit 9. Said recovery unit 9 produces a low-grade steam 10 by evaporating a feed water 14. Said steam 10 has a temperature not greater than 200° C., preferably in the range 150-200° C., and is used in at least one of the TUs 3 of the ammonia section 1. The cooled exhaust gas leaves the recovery unit 9 at line flow 11.

A particularly preferred use for low-grade steam 10 is regeneration of $CO_2$ removal solution in the $CO_2$ removal unit of the purification section. Removal of carbon dioxide is preferably carried out with any of the following methods: amines, or activated amines, or potassium carbonate.

Since the gas engine exhaust gas 8 is usually at a higher temperature (e.g. 350-400° C.), the heat recovery unit may also provide an additional amount of mechanical or electrical power, as indicated by line 13, for example via a heat recovery steam generator (HRSG) and a backpressure or extraction steam turbine.

In a preferred embodiment, the global steam-to-carbon ratio in the front-end section of the plant 1 is regulated at a low value of less than 2.7, preferably in the range 2-2.6 and more preferably in the range 2.3-2.6. As stated above, the reduction of said ratio has a positive and synergistic effect with the provision of the gas engine(s) 6 and of the heat recovery unit 9.

The global steam-to-carbon ratio can be reduced in conjunction with one or more of the following: by installing a pre-reformer upstream the primary reformer; bypassing a portion of natural gas (typically more than 10% of the reformer feed) around the steam reformer tubes and sending it directly to the secondary reformer.

In some embodiments, the ammonia-urea plant 1 comprises a hydrogen recovery unit (HRU). The tail gas 12 of said HRU may be used as fuel in the gas engine(s) 6 as shown in FIG. 1. For a revamp, this is very convenient compared to the recycle in the steam reformer, because it avoids the otherwise typically necessary modification of the steam reformer burners. This is possible even if the tail gas of the HRU is at low pressure, such as for instance from a cryogenic HRU or a PSA.

Additional steam 4 for the thermal users 3 can be optionally provided by a gas-fired auxiliary boiler 5.

Further preferred aspects of the invention are the following. Energy can be saved by installing a means for recovering reactants (H2 and N2) from the synthesis loop purge, while effectively rejecting the inerts (Ar and especially CH4). Such means may include a membrane, or on adsorbents, or preferably a cryogenic HRU which recovers most of the reactants at a pressure preferably of at least 60 bar and preferably more than 100 bar.

Both reducing the S/C ratio alone and installing a purge gas recovery HRU alone provides some energy saving, but there is synergy in applying both solutions together.

In fact, a lower S/C ratio reduces the methane conversion in the reforming process, increasing the residual methane concentration in the make-up gas and ultimately in the synthesis loop. This offsets saving in process steam consumption. However, coupling an HRU with a lower S/C ratio eliminates the drawbacks of the latter, i.e. the increased methane concentration in the synthesis loop, while retaining the benefits of both: reduced firing, less inerts in the synthesis loop, H2 and N2 recovered at high pressure.

Depending on the selected S/C ratio, either a high temperature (HTS) or a medium temperature (MTS) shift may be deployed. A HTS allows recover of a higher level heat, hence ensuring a higher overall efficiency and less gas consumption. However, HTS can be used only down to a global S/C ratio of about 2.6-2.7. In some cases it may be useful to reduce the S/C ratio to lower values, hence MTS is then required. The MTS can be adiabatic or isothermal. Isothermal MTS means that the shift converter contains a heat exchanger adapted to keep the temperature of the shift converter product gas within a desired range. Adiabatic MTS can be used when the amount of heat released in the shift converter is limited, for example when the oxidant in the secondary reformer is air and the concentration of CO inlet to the shift is not too high.

The invention claimed is:

1. A process for producing ammonia and a derivative of ammonia from a natural gas feed (NG) comprising:
    converting of the natural gas feed into synthesis gas in a front-end section;
    synthesizing ammonia from said synthesis gas in a synthesis loop;
    using at least part of said ammonia to produce said derivative of ammonia,
    said process being carried out with power users requiring a mechanical power for operation, and thermal users requiring a heat input for operation;
    wherein:
    a portion of said natural gas feed is used to fuel a reciprocating gas engine;
    power produced by said gas engine is used to cover at least partially the power demand of said power users;
    heat is recovered from an exhaust gas of said gas engine, and at least part of said heat is recovered, to provide heat to at least one of said thermal users,
    wherein the heat recovered from said exhaust gas of said gas engine is at least in part low grade heat and the low grade heat is transferred to at least one of said thermal users via a heat exchange medium, said medium being heated by indirect heat exchange with the exhaust gas to a temperature which is not greater than 200° C.

2. The process according to claim 1, wherein said power is transferred from said gas engine to at least one of said power users in an electrical or mechanical form.

3. The process according to claim 1, wherein said conversion of natural gas into synthesis gas in said front-end section is carried out by steam reforming with a global steam-to-carbon molar ratio not greater than 2.7.

4. The process according to claim 1, wherein said heat exchange medium is water or oil, natural gas or other fuel, process air or combustion air.

5. The process according to claim 1, wherein:
    a first portion of heat recovered from exhaust of said gas engine is used in a heat recovery steam generator to produce steam and said steam is expanded in a backpressure or extraction steam turbine producing further mechanical power, thus forming a combined cycle, and
    a second portion of heat recovered from the exhaust gas of said gas engine is used to provide said low-grade heat.

6. The process according to claim 5, wherein a steam flow taken from said backpressure or extraction steam turbine is used to provide heating to at least one of said thermal users.

7. The process according to claim 1, wherein converting the natural gas feed into synthesis gas comprises feeding the natural gas feed to a primary steam reformer and a secondary reformer;
    an autothermal reformer;
    or a partial oxidation reactor, obtaining a raw synthesis gas, and purifying the raw synthesis gas, wherein the purification comprises at least a shift reaction and removal of carbon dioxide from the shifted gas.

8. The process according to claim 7, wherein the shift reaction comprises a high temperature shift (HTS) on an iron-based catalyst, or a medium temperature shift (MTS) on a copper-based catalyst.

9. The process according to claim 7, wherein the removal of carbon dioxide is carried out by absorption using any of the following absorbents: amines, or activated amines, or potassium carbonates.

10. The process according to claim 1, wherein said derivative of ammonia is urea.

11. The process according to claim 1, in which said power users are at least one of a compressor, a fan or a pump.

12. The process according to claim 1, further comprising a fired reformer or other fired heater, wherein said exhaust gas from said gas engine is used to supply in part a combustion medium for a fired reformer or other fired heater.

13. The process according to claim 1, wherein part of the fuel for the gas engine is a waste fuel stream.

14. A plant for producing ammonia and a derivative of ammonia, said plant comprising:
    a front-end section for generation of ammonia make-up synthesis gas;
    a synthesis loop for synthesis of ammonia from said make-up synthesis gas;
    a section for the conversion of at least part of the synthesized ammonia into said derivative;
    power users requiring a mechanical power for operation, and at least one thermal user requiring a heat input for operation;
    wherein said plant further comprises:
    at least one reciprocating gas engine, the power produced by said gas engine being transferred to at least one of said power users,
    heat recovery section for recovery of low-grade heat from exhaust gas of said gas engine, wherein the low-grade heat is transferred to at least one of said thermal users via indirect heat exchange with a heat exchange medium,
    wherein the heat exchange medium is heated by the exhaust gas to a temperature not greater than 200° C.

15. A method of modernizing a plant for producing ammonia and a derivative of ammonia, comprising the steps of:
providing a plant that comprises:
a front-end section for generation of ammonia make-up synthesis gas;
an ammonia synthesis loop for synthesis of ammonia from said make-up synthesis gas;
an ammonia conversion section for the conversion of at least part of the synthesized ammonia into said derivative; and
power users and thermal users;
providing to the plant at least one reciprocating gas engine and a suitable power transfer section to transfer the power produced by said engine to at least one of said power users, and
providing to the plant a heat recovery section for recovery of low-grade heat from exhaust gas of said gas engine, wherein the low-grade heat is transferred to at least one of said thermal users via indirect heat exchange with a heat exchange medium, wherein the heat exchange medium is heated by the exhaust gas to a temperature not greater than 200° C.

16. The method according to claim 15, wherein the power transfer section comprises: an electrical motor and an electrical generator coupled to said gas engine.

17. The method according to claim 16, wherein at least one thermal user is one of the following:
a reboiler of a $CO_2$ rich solution in a $CO_2$ removal unit,
a reboiler of an absorption refrigeration chiller,
a reboiler of an ammonia-rich aqueous ammonia solution distillation system,
a preheater of a natural gas or fuel gas, or
a preheater of process air or a preheater of combustion air.

18. The method according to claim 15, further comprising the step of reducing a global steam-to-carbon ratio of the front-end section to a value lower than the original.

19. The process according to claim 1, wherein said conversion of natural gas into synthesis gas in said front-end section is carried out by steam reforming with a global steam-to-carbon molar ratio in the range 2.3 to 2.6.

20. The method according to claim 18, wherein said global steam-to-carbon ratio of the front-end section is in a range of 2.3 to 2.6.

21. The process according to claim 13, wherein part of said waste fuel stream is a purge gas taken from said ammonia synthesis loop.

22. The process according to claim 1, wherein said at least one of said thermal users is a $CO_2$ removal unit, an absorption refrigeration chiller or an ammonia distillation system.

* * * * *